United States Patent
Buchecker et al.

(10) Patent No.: US 6,225,479 B1
(45) Date of Patent: *May 1, 2001

(54) OPTICALLY ACTIVE BIS-DIOXANE DERIVATIVES

(75) Inventors: Richard Buchecker, Zürich; Jürg Fünfschilling, Basel, both of (CH)

(73) Assignee: Rolic AG, Basel (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/756,925

(22) Filed: Dec. 2, 1996

(30) Foreign Application Priority Data

Jan. 2, 1996 (CH) .......................................................... 3/96

(51) Int. Cl.[7] .................................................. C07D 407/10
(52) U.S. Cl. ...................................... 549/370; 252/299.61
(58) Field of Search ........................ 549/370; 252/299.61

(56) References Cited

U.S. PATENT DOCUMENTS

| | | | |
|---|---|---|---|
| 4,704,227 | 11/1987 | Krause et al. | 252/299.61 |
| 4,726,911 | 2/1988 | Krause et al. | 252/299.61 |
| 5,302,317 | 4/1994 | Boller et al. | 252/299.6 |
| 5,494,606 | 2/1996 | Reiffenrath et al. | 252/299.61 |
| 5,518,653 | 5/1996 | Buchecker et al. | 252/299.61 |
| 5,547,605 | 8/1996 | Fuss et al. | 252/299.6 |
| 5,688,437 | * 11/1997 | Sato et al. | 252/299.61 |

FOREIGN PATENT DOCUMENTS

| | | |
|---|---|---|
| 3 715 029 | 11/1987 | (DE) . |
| 0 122 389 | 10/1984 | (EP) . |
| 0 154 840 | 9/1985 | (EP) . |
| 0 182 054 | 5/1986 | (EP) . |
| 0 315 014 | 5/1989 | (EP) . |
| 0 457 105 | 11/1991 | (EP) . |
| 4 444 701 | 6/1995 | (EP) . |
| 0 732 330 | 9/1996 | (EP) . |
| 2190675 | 11/1987 | (GB) . |
| 91/16321 | 10/1996 | (WO) . |

OTHER PUBLICATIONS

Mol. Cryst. Liq. 204, (1991) 37–42.

Abstract corresponding to EP 0732330, AN 96–414414/42, 1996, C96–130603.

Tetrahedron Letters 35, pp. 3277–3280 (1994).

Mol Cryst. Liq. Cryst. 213, pp. 259–267 (1992).

Mol Cryst. Liq. Cryst. vol. 131 pp. 327–342 (1985).

Abstract corresponding to EP 0 122 389, C84–112032, 1984.

Abstract corresponding to EP 457 105, C91–147362, 1991.

\* cited by examiner

*Primary Examiner*—Laura L. Stockton
(74) *Attorney, Agent, or Firm*—Finnegan, Henderson, Farabow, Garrett, & Dunner L.L.P.

(57) ABSTRACT

A compound of formula

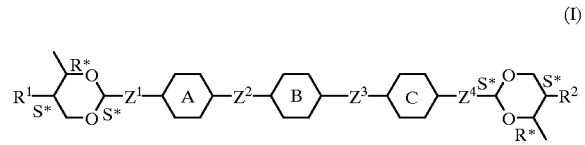

(I)

in which

R[1] and R[2] each independently represent and alkyl or alkenyl group in which one or more hydrogen atoms is optionaly substituted by fluorine, chlorine, or cyano; and in which optionally one or more non-adjacent methylene groups are optionaly replaced by —O—, —COO— or —OOC—;

$Z^1$ to $Z^4$ each independently represent a single bond, —CH$_2$CH$_2$—, —CH$_2$O—, —OCH$_2$—, —C≡C—, —(CH$_2$)$_4$—, —(CH$_2$)$_3$O—, —CH=CH—CH$_2$O—, OCH$_2$—, —CH=CH—, —CH=CH—(CH$_2$)$_2$— or —(CH$_2$)$_2$—CH=CH—, with the proviso firstly that the oxygen atom is not linked directly with the chiral dioxane ring and secondly $Z^2$ and $Z^3$ may also represent —COO— or —OOC—;

R* and S* signify that the denoted carbon have the (R) or (S) configuration respectively or the optical antipode thereof; and one of A, B and C is a 1,4-phenylene which is optionally substituted with 1 or 2 fluorine atoms, pyridine-2,5-diyl or pyrimidine-2,5-diyl and the other two rings are each independently 1,4-phenylene which is optionally substituted by one or more a fluorine atoms or trans-1,4-cyclohexylene;

liquid crystalline mixtures containing said compounds and the use of said compounds for electro-optical purposes.

16 Claims, No Drawings

OPTICALLY ACTIVE BIS-DIOXANE DERIVATIVES

FIELD OF THE INVENTION

The invention relates to optically active bis-methyldioxanes, liquid crystalline mixtures which contain such compounds, the use of such compounds and mixtures for optical and electro-optical devices, and electro-optical devices containing one or more of such compounds.

BACKGROUND OF THE INVENTION

Liquid crystals are used primarily as dielectrics in display devices, since the optical properties of such substances can be influenced by an applied voltage. Electro-optical devices based on liquid crystals are known and are based on various effects. Such devices are, for example, cells having dynamic scattering, DAP cells (deformation of aligned phases), guest/host cells, TN cells having a "twisted nematic" structure, STN cells ("super twisted nematic"), SBE cells ("super birefringence effect") and OMI cells ("optical mode interference"). Displays having a high content of information actively controlled cells, for example, TFT cells ("thin film transistor"), have in particular recently become important in addition to the passively controlled, multiplexed cells. In addition to the aforementioned cell types, which are based on the use of nematic or cholesteric liquid crystals, cell types which are based on the principle of chiral tilted smectic phases are known. Thereto there belong SSF cells (surface stabilized ferroelectric), SBF cells (short-pitch bistable ferroelectric) or DHF cells (deformed helix ferroelectric). For these cells types there are generally preferred as tilted smectic phases chiral smectic C ($S_C^*$) phases, which permit especially large response speeds.

Materials for display devices based on chiral tilted smectic phases can preferably consist of a material having a tilted smectic phase, usually a $S_C$ phase, and one or more optically active dopants. The use of such chiral dopants in ferroelectric liquid crystals primarily serves to produce or alter a twisting of the tilted smectic phase and to induce a spontaneous polarization. The chiral dopants should have an adequate thermal and photochemical stability, should have a good compatibility with the tilted smectic liquid crystals, should have a viscosity which is as low as possible and should not limit the mesophase range too severely. Further, a spontaneous polarization which is as high as possible and, depending on the cell type, a rather small twisting capacity (SSF cells) or a twisting capacity which is as high as possible (SBF, DHF cells) is desirable.

As chiral dopants there also come into consideration in principle compounds which themselves have no tilted phase or generally no mesophase. This is especially frequent in the case of dopants having a very high twisting capacity. However, such dopants usually have the disadvantage that they severely narrow the tilted phase range of post mixtures to which they are added. Accordingly, dopants have been sought which do not have this disadvantage or which have this disadvantage only to a small extent.

SUMMARY OF THE INVENTION

Compounds having the formula

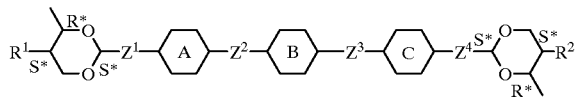

wherein $R^1$ and $R^2$ each independently are alkyl or alkenyl; alkyl or alkenyl in which one methylene group is replaced by —O—, —COO—, or —OOC—; alkyl or alkenyl in which two non-adjacent methylene groups are replaced by —O—, —COO—, or —OOC—; alkyl or alkenyl in which at least one hydrogen atom is replaced by fluorine, chlorine, or cyano; alkyl or alkenyl in which one methylene group is replaced by —O—, —COO—, or —OOC— and at least one hydrogen atom is replaced by fluorine, chlorine, or cyano; or alkyl or alkenyl in which two non-adjacent methylene groups are replaced by —O—, —COO—, or —OOC— and at least one hydrogen atom is replaced by fluorine, chlorine or cyano;

one of rings A, B and C is a 1,4-phenylene which is unsubstituted or substituted with 1 or 2 fluorine atoms, pyridine-2,5-diyl or pyrimidine-2,5-diyl and the other two rings each independently are 1,4-phenylene which is unsubstituted or substituted with 1 or 2 fluorine atoms or trans-1,4-cyclohexylene;

$Z^1$ and $Z^4$ each independently are a single bond, —CH$_2$CH$_2$—, —CH$_2$O—, —OCH$_2$—, —C≡C—, —(CH$_2$)$_4$—, —(CH$_2$)$_3$O—, —O(CH$_2$)$_3$—, —CH=CH—CH$_2$O—, —OCH$_2$—CH=CH—, —CH=CH—(CH$_2$)$_2$— or —(CH$_2$)$_2$CH=CH—, with the proviso that the oxygen atom is not linked directly with the chiral dioxane ring;

$Z^2$ and $Z^3$ each independently are a single bond, —CH$_2$—CH$_2$—, —O—CH$_2$—, —CH$_2$—O—, —COO—, —OOC—, —C≡C—, —(CH$_2$)$_4$—, —O(CH$_2$)$_3$—, —(CH$_2$)$_3$O—, —CH=CH—CH$_2$O—, —OCH$_2$—CH=CH—, —(CH$_2$)$_2$—CH=CH— or —CH=CH—(CH$_2$)$_2$—; and R* and S* signify that the denoted carbon have the (R) configuration or its optical antipode or the (S) configuration or its optical antipode.

The compounds of formula I, which have a high twisting capacity and a comparatively high spontaneous polarization, also have mostly smectic mesophases, partially even $S_C^*$ phases at comparatively high temperatures. In mixtures with $S_C$ basic mixtures they give rise to no lowering or only to a relatively small lowering of the $S_C^*$ phase. In spite of their basic structure comprising five rings they have a surprisingly good solubility in $S_C$ basic mixtures. Having regard to these properties, they are suitable as dopants for use in ferroelectric cells, especially in DHF cells. Moreover, they can also be used for cholesteric mixtures, especially in applications as cholesteric filters or as polarizers.

DETAILED DESCRIPTION OF THE INVENTION $R^1$ and $R^2$ embrace straight-chain and branched (optionally chiral) groups such as alkyl, 2-alkenyl, 3-alkenyl, 4-alkenyl, alkenyl having a terminal double bond, alkoxyalkyl, alkenyloxyalkyl, alkylcarbonyloxyalkyl, alkoxycarbonylalkyl, fluoroalkyl, difluoroalkyl, trifluoroalkyl, chloroalkyl, cyanoalkyl, 1-methylalkyl, 2-methylalkyl and the like, in each case with a maximum of 16 carbon atoms, preferably a maximum of 12 carbon atoms.

4-phenylene and the other two rings each independently signify 1,4-trans-cyclohexylene, 1,4-phenylene, 2- or 3-fluoro-1,4-phenylene or 2,3-difluoro-1,4-phenylene.

Quite especially preferred compounds are those of the formulas

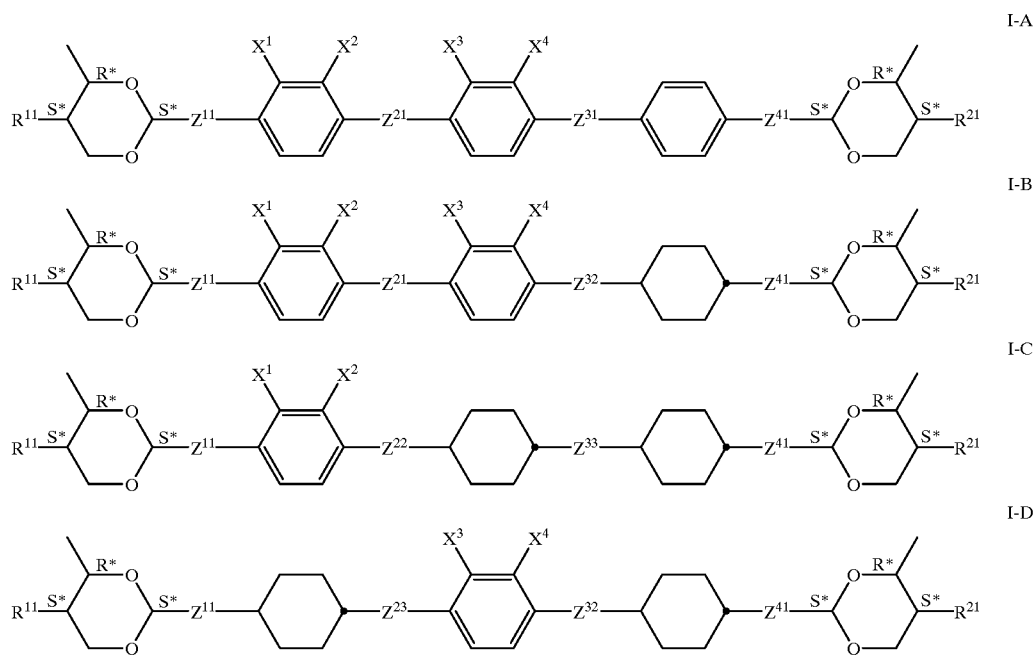

wherein $R^{11}$ and $R^{21}$ each independently are $C_1$–$C_{12}$ alkyl or $C_2$–$C_{12}$ alkenyl; or $C_1$–$C_{12}$ alkyl or $C_2$–$C_{12}$ alkenyl in which one methylene group is replaced by —O—, —COO— or —OOC—;

$Z^{11}$, $Z^{33}$ and $Z^{41}$ each independently are a single bond or —CH$_2$CH$_2$—;

$Z^{21}$ and $Z^{31}$ each independently are a single bond, —COO— or —OOC—;

$Z^{22}$ and $Z^{32}$ each independently are a single bond, —CH$_2$CH$_2$— or —OCH$_2$—;

$Z^{23}$ is a single bond, —CH$_2$CH$_2$— or —CH$_2$O—; and the substituents $X^1$ to $X^4$ each independently are hydrogen or fluorine.

Examples of preferred groups are methyl, ethyl, propyl, butyl, pentyl, hexyl, heptyl, octyl, nonyl, decyl, undecyl, dodecyl, 1-methylpropyl, 1-methylheptyl, 2Z-pentenyl, 2Z-hexenyl, 2Z-heptenyl, 2Z-octenyl 3E-pentenyl, 3E-hexenyl, 3E-heptenyl, 3E-octenyl, 5E-octenyl, 3-butenyl, 4-pentenyl, 5-hexenyl, 6-heptenyl, 7-octenyl, methoxyethyl, methoxypropyl, methoxybutyl, ethoxyethyl, propyloxyethyl, 2-fluoropropyl, 2-fluoropentyl, 2-fluorooctyl, 2-chlorohexyl, 2-chlorooctyl and the like.

The term "1,4-phenylene which is unsubstituted or substituted with 1 or 2 fluorine atoms" signifies 1,4-phenylene, 2- or 3-fluoro-1,4-phenylene, 2,3-difluoro-1,4-phenylene, 2,6- or 3,5-difluoro-1,4-phenylene. Preferred fluorine-substituted rings are 2- or 3-fluoro-1,4-phenylene or 2,3-difluoro-1,4-phenylene.

Preferred compounds of formula I are those in which $Z^1$ and $Z^4$ signify a single bond, —CH$_2$CH$_2$—, —CH$_2$O— or —OCH$_2$—; and $Z^2$ and $Z^3$ signify a single bond, —CH$_2$CH$_2$—, —CH$_2$O—, —OCH$_2$—, —COO— or —OOC—, with the oxygen atom present in groups $Z^1$ to $Z^4$ preferably being linked with an aromatic ring. In especially preferred compounds, no more than two of the groups $Z^1$, $Z^2$, $Z^3$ and $Z^4$ are other than a single bond.

Also, preferred compounds of formula I are those in which rings A, B and C each independently signify 1,4-phenylene, 2- or 3-fluoro-1,4-phenylene or 2,3-difluoro-1,4-phenylene; or one of rings A, B and C signifies 1,4-phenylene, 2- or 3-fluoro-1,4-phenylene or 2,3-difluoro-1, The relative configurations of the chiral carbon atoms denoted by (S*) and (R*) in formula I and the subsequent formulas signify that the denoted carbon atoms as indicated have the (S) or (R) configuration or that all denoted carbon atoms have the mirror image configuration. The formulas accordingly embrace in each case the diastereoisomer in which (S*) stands for the (S) configuration and (R*) stands for the (R) configuration as well as its optical antipode in which (S*) stands for the (R) configuration and (R*) stands for the (S) configuration.

In particular, the compounds of the following formulas are preferred:

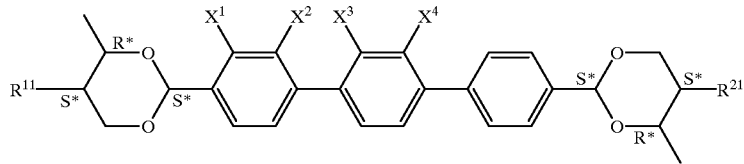
I-1
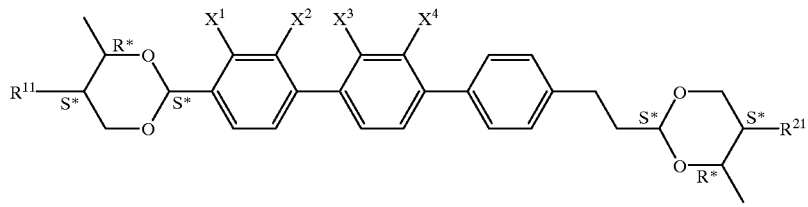
I-2
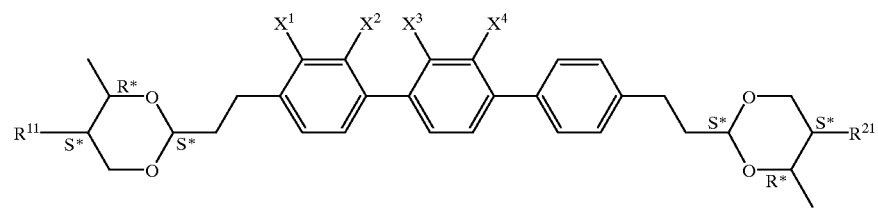
I-3
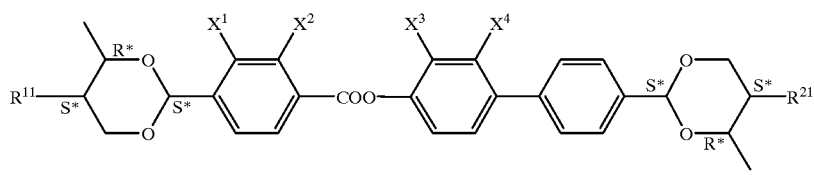
I-4
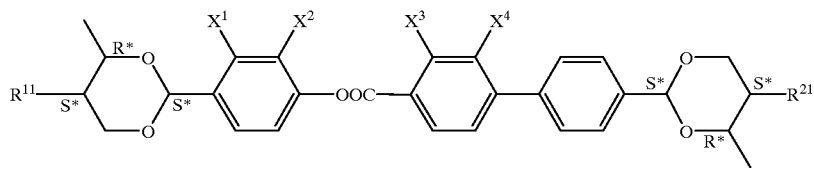
I-5
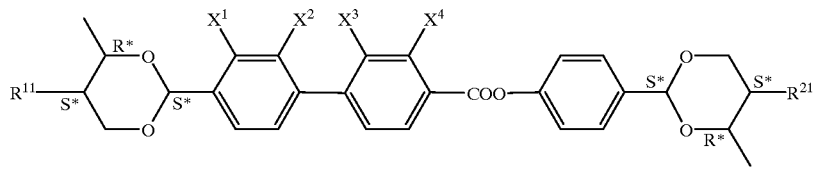
I-6
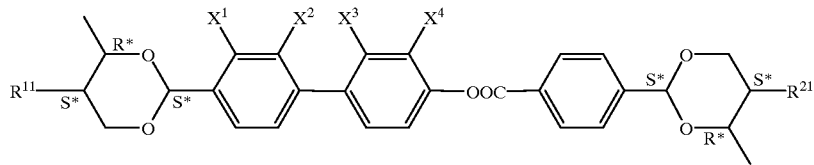
I-7
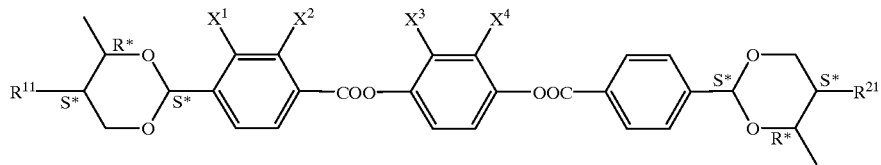
I-8

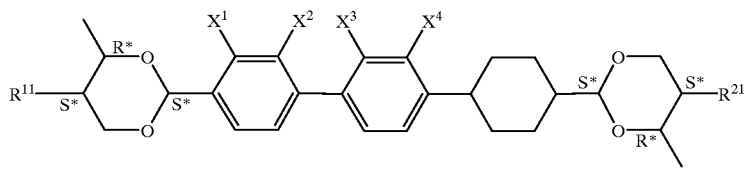
I-9
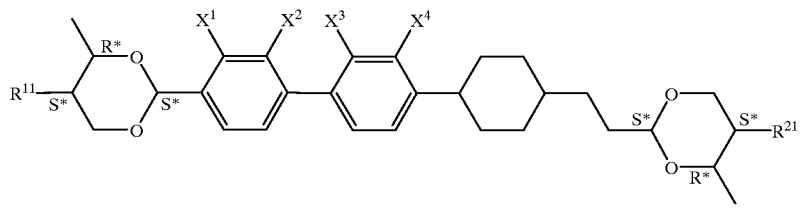
I-10
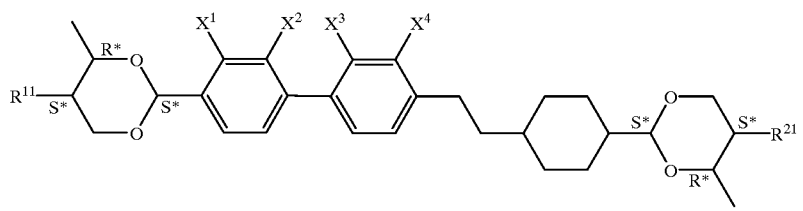
I-11
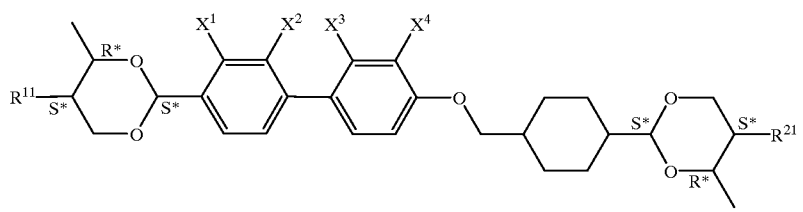
I-12
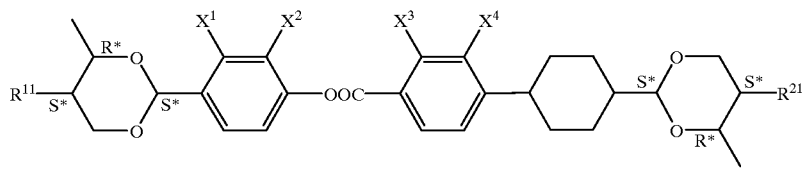
I-13
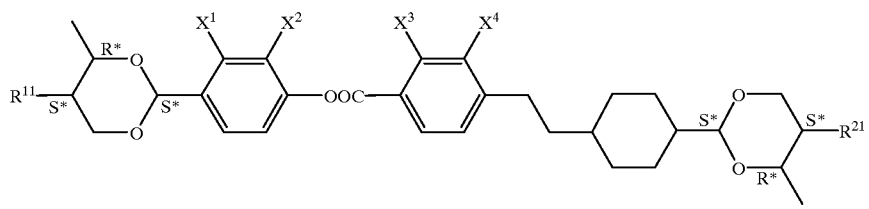
I-14
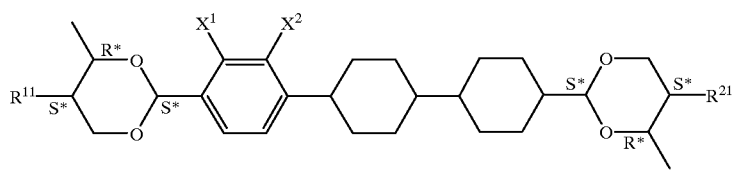
I-15

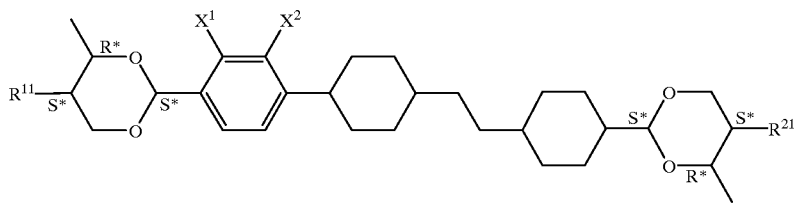
I-16
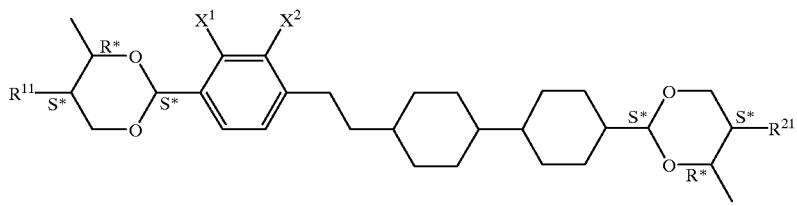
I-17
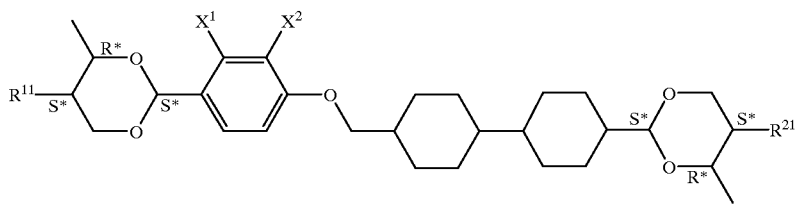
I-18
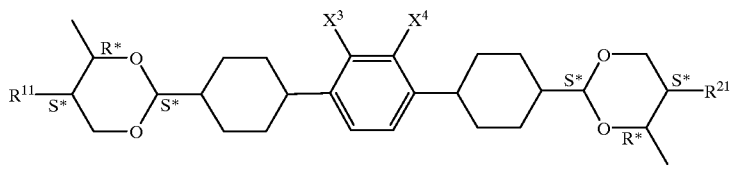
I-19
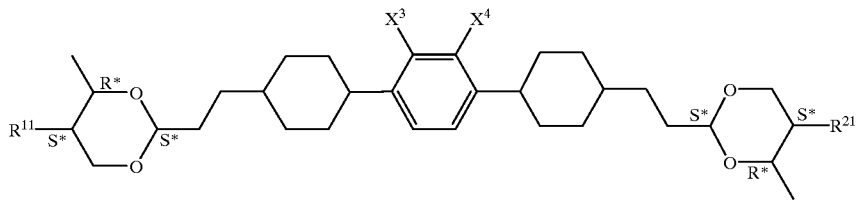
I-20
wherein
$R^{11}$ and $R^{21}$ are as described above; and
$X^1$ to $X^4$ are, independently, hydrogen or fluorine.
Preferably in each case no more than two, and more preferably one, of the substituents $X^1$ to $X^4$ are different from hydrogen.
The compounds of formula I can be produced in a known manner, for example in accordance with Scheme 1.
Scheme 1
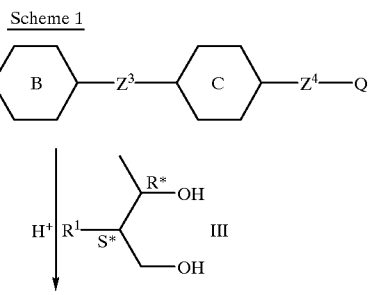

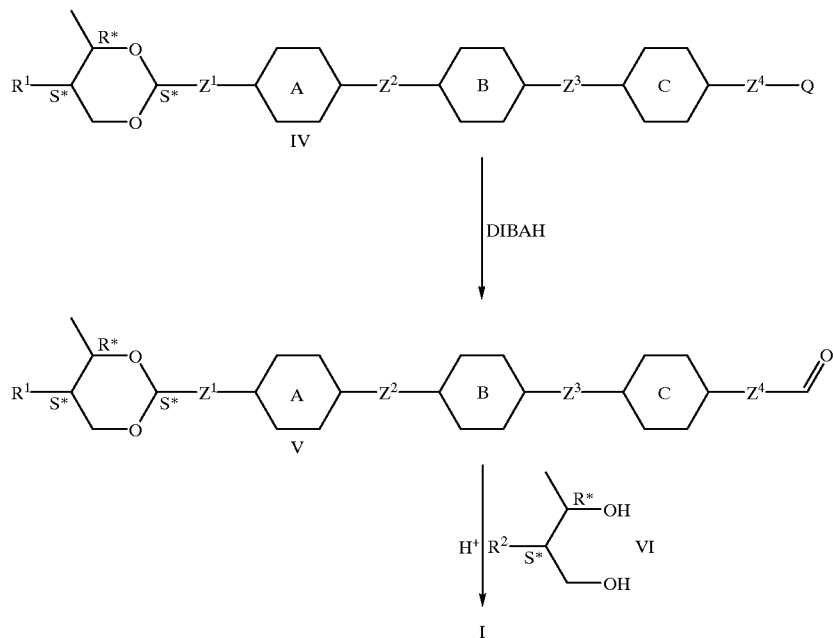

wherein

Q is —CN or —COOR;

R is $C_1$–$C_7$ alkyl such as methyl, ethyl, propyl, i-propyl, butyl, 2-butyl or tert.-butyl;

and the remaining symbols are as described above.

Thus, an aldehyde of formula II, which contains a second group Q readily convertible into an aldehyde, is firstly reacted with a diol of formula III to give a monoacetal of formula IV. Thereafter, the nitrile or the ester of formula IV is converted by reduction, for example with diisobutylaluminium hydride (DIBAH), into an aldehyde of formula V which, by a second acetalization with a diol of formula VI, gives the diacetal of formula I.

When ester groups are present in $R^1$ and/or $R^2$, the esterification is preferably not carried out until the dioxane rings have been formed. Further, when $R^1$ and/or $R^2$ contain ether groups, the etherification can also be effected, if desired, after formation of the dioxane rings.

Compounds of formula I in which $Z^2$ and/or $Z^3$ signify an ester group are preferably produced by esterifying corresponding partial structures having pre-formed dioxane rings.

Furthermore, those compounds of formula I which contain two adjacent directly linked phenyl rings can be produced by palladium-catalyzed coupling, for example, of an appropriately substituted aromatic halide or sulfonate of formula VII with an appropriately substituted arylboric ester of formula VII (see Scheme 2). Such couplings are known, for example, in Tetrahedron Letters 35, 3277 (1994).

Scheme 2

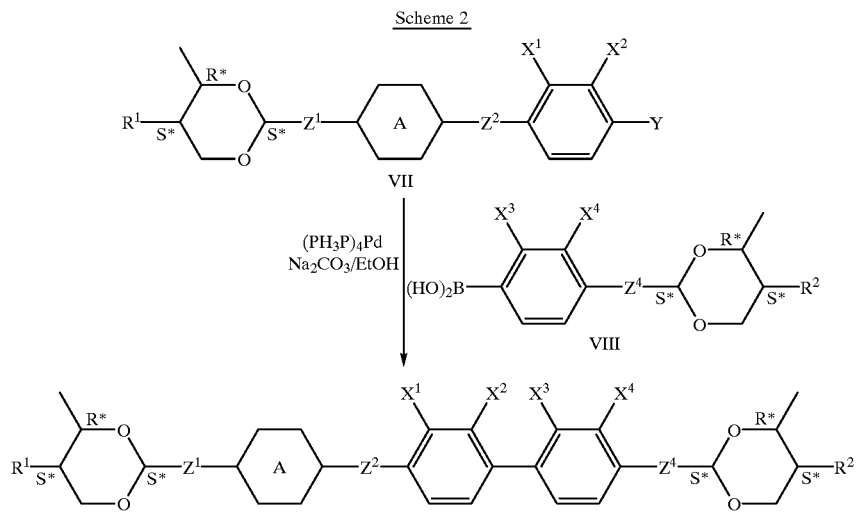

wherein

Y signifies Br, I or —OSO$_2$CF$_3$; and the remaining symbols have the above significance.

The starting materials required for the synthesis of the compounds of formula I are known or are analogues of known compounds. Thus, for example, numerous nitriles or esters of formula II are known as intermediates in the synthesis of liquid crystals, for example in EP-A-0 122 389. The preparation of the diols of formula III is also known, for example in Mol Cryst. Liq. Cryst 213, 159 (1992).

The analogues of the starting materials of formulas VII or VIII, for example compounds having an achiral dioxane or dioxolane ring, which usually serves as a protecting group, are also known. Linkage reactions of rings by ester formation, ether formation or by direct aromatic couplings via boric acids, as described, for example, in Tetrahedron Letters, 35, 3277 (1994), are known. These reactions belong to standard methods in the synthesis of liquid crystals and are known.

The compounds in accordance with the invention are useful as chiral dopants for liquid crystalline mixtures. The invention is therefore also concerned with liquid crystalline mixtures having at least two components, with at least one of the components being an optically active compound of formula I.

Preferably, the mixtures in accordance with the invention contain a single liquid crystalline compound or a liquid crystalline mixture as the carrier material and one or more optically active compounds of formula I. Suitable carrier materials are in principle all liquid crystal materials which have a twistable liquid crystal phase with an adequate mesophase range. As mentioned, the liquid crystalline carrier material can be a single compound or a mixture and preferably has a clearing point of at least about 60° C. The compounds of formula I are especially suitable as chiral dopants for carrier materials having a nematic, cholesteric or tilted smectic phase, especially for carrier materials having an achiral or chiral smectic C phase. Suitable liquid crystal components are known in large numbers, for example, from D. Demus et al., Flüssige Kristalle in Tabellen, VEB Deutscher Verlag für Grundstoffindustrie, Leipzig, volumes I and II, or from Landolt-Börnstein, Liquid Crystals, volume IV 7a–d, and many of them are, moreover, commercially available.

The content of chiral dopant of formula I is determined largely by the twisting capacity, the spontaneous polarization and the desired pitch. The content of chiral dopant can accordingly vary in a wide range according to use and can be, for example, about 0.1–40 wt. %. In general, a content of about 1–30 wt. % especially of about 3–25 wt. %, of optically active dopants of formula I is preferred for display devices based on liquid crystals having tilted smectic phases.

Preferably, the mixtures in accordance with the invention contain, in addition to one or more compounds of formula I, one or more compounds from the group of compounds of the formulas

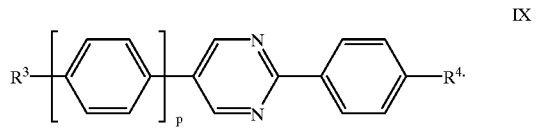

IX

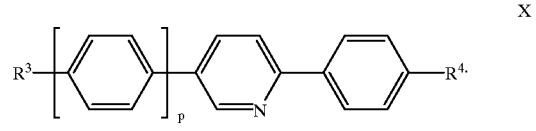

X

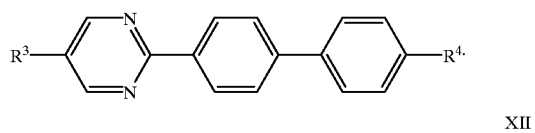

XI

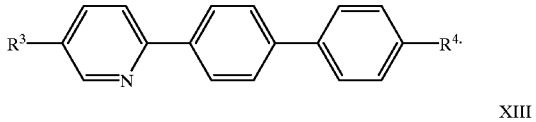

XII

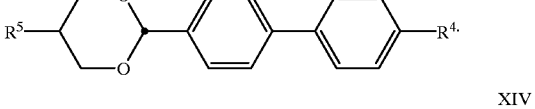

XIII

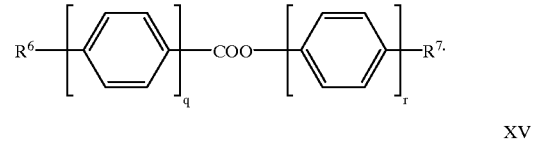

XIV

XV

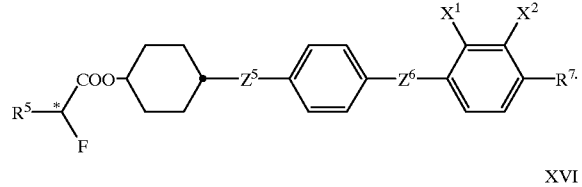

XVI

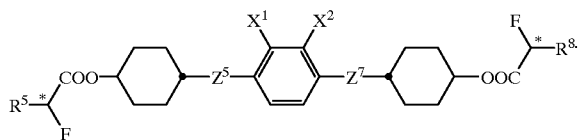

XVII

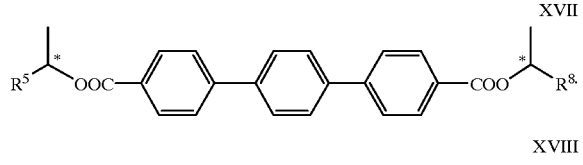

XVIII

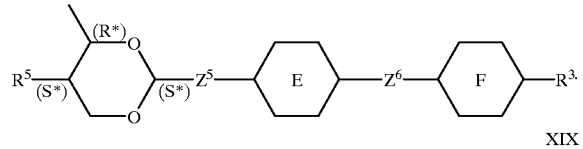

XIX

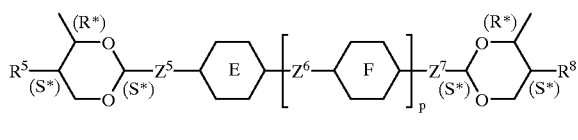

wherein p signifies 0 or 1;

q and r each independently signify 1 or 2, whereby q+r=2 or 3;

$R^3$ and $R^4$ each independently signify alkyl, alkenyl, alkoxy, alkenyloxy, alkoxyalkyl, alkoxyalkoxy, alkanoyloxy, alkenoyloxy, alkoxycarbonyl, alkenyloxycarbonyl;

$R^5$ and $R^8$ each independently signify alkyl or alkenyl, $R^6$ and $R^7$ each independently signify alkyl, alkenyl, alkoxy and/or alkenyloxy;

$Z^5$, $Z^6$ and $Z^7$ each independently signify a single bond, —CH$_2$CH$_2$— or —CH$_2$O—, and $Z^6$ also signifies —OCH$_2$—, —COO— or —OOC—;

E and F each independently signify phenylene-1,4-diyl or cyclohexylene-1,4-diyl;

$X^1$ and $X^2$ each independently signify hydrogen or fluorine; and (R*) and (S*) signify the relative configurations.

The compounds of formulae XV to XIX are optically active dopants which, depending on the desired effect, can be present in the mixture in one of the two enantiomeric forms in addition to one or more compounds of formula I.

The substituents $R^3$ to $R^8$ have a maximum of in each case 18 carbon atoms, preferably 5–12 carbon atoms. They can be straight-chain or branched, but are are preferably straight-chain.

Electro-optical devices containing one or more compounds of formula I are also an object of the present invention. The production of the liquid crystalline mixtures and of the electro-optical devices can be effected in a known manner.

The production of the compounds of formula I and of liquid crystalline mixtures containing these compounds are illustrated in more detail by the following Examples. Optical antipodes of the compounds of formula I have in each case the same phase transition temperatures and induce the same absolute values of the spontaneous polarization and of the twisting, but with opposite signs. The abbreviations used for the characterization of the phase transitions have the following significances:

C crystalline,

S smectic, $S_A$, $S_B$, $S_C$ etc. smectic A, B, C etc., $S_A^*$, $S_F^*$ etc. chiral smectic C, F etc.

N nematic,

N* cholesteric, and

I isotropic.

EXAMPLE 1 a) A mixture of 0.80 g of 4-cyano-4'-(trans-4-formyl-cyclohexyl)biphenyl (preparation see. Mol Cryst. Liq. Cryst. Vol. 131, 327 (1985)), 0.587 g of (2R,3S)-2-octyl-1,3-butanediol (preparation see EP-0 457 105) 40 ml of toluene and 8 drops of 2N sulfuric acid was heated under reflux in a round flask having a magnetic stirrer, water separator and condenser under nitrogen for 15 hours. Then, the mixture was cooled to room temperature, 30 drops of triethylamine were added and the mixture was partitioned between diethyl ether and saturated sodium bicarbonate solution. The organic phases were separated thereupon dried over magnesium sulfate, filtered and the filtrate was evaporated. This gave 1.4 g of crude 4'-{trans-4-[(2R,3S,5R)-5-octyl-4-methyl-1,3-dioxan-2-yl]cyclohexyl}-4-cyanobiphenyl as a light yellowish solid.

b) 1.4 g of 4'-{trans-4-[(2R,3S,5R)-5-octyl-4-methyl-1,3-dioxan-2-yl]cyclohexyl}-4-cyanobiphenyl were dissolved in 30 ml of toluene, cooled to 0° C. and treated dropwise with 3.2 ml of DIBAH solution (20% in toluene) within 3 minutes. The reaction mixture was warmed to room temperature and stirred at this temperature for 15 hours. Thereafter, the mixture was partitioned between diethyl ether and water, the ether phases were poured into 80 ml of water, the mixture was cooled to 0° C. and treated dropwise with 1N hydrochloric acid while stirring vigorously until the pH was 2. The mixture was transferred to a separating funnel, the aqueous phase was separated and the organic phase was washed immediately with saturated sodium bicarbonate solution. The ether phase was dried over magnesium sulfate, filtered and the filtrate was evaporated. This gave 1.37 g of crude 4'-{trans-4-[(2R,3S,5R)-5-octyl-4-methyl-1,3-dioxan-2-yl]cyclohexyl}biphenyl-4-carboxaldehyde as a yellow solid.

c) A solution of 1.37 g of 4'-{trans-4-[(2R,3S,5R)-5-octyl-4-methyl-1,3-dioxan-2-yl]cyclohexyl}biphenyl-4-carboxaldehyde and 0.61 g of (2R,3S)-2-octyl-1,3-butanediol in 40 ml of toluene was treated with 8 drops of 2N sulfuric acid in a round flask having a magnetic stirrer, water separator and condenser under nitrogen and stirred under reflux for 2.5 hours. Then, the mixture was cooled to room temperature, 30 drops of triethylamine were added and the reaction mixture was partitioned between diethyl ether and saturated sodium carbonate solution. The organic phases were dried over magnesium sulfate, filtered, the filtrate was evaporated and the residue was chromatographed on 140 g of silica gel with toluene/ethyl acetate (50:1). Three-fold crystallization from hexane gave 0.95 g of pure 4'-{trans-4-[(2R,3S,5R)-5-octyl-4-methyl-1,3-dioxan-2-yl]cyclohexyl}-4-[(2R,3S,5R)-5-octyl-4-methyl-1,3-dioxan-2-yl]biphenyl as colourless crystals m.p. (C/$S_B$): 73.5° C., $S_B/S_A$: 75.5° C., $S_A/N^*$: 106° C., cl.p. (N*/I): 219° C., [α]$_D$ (CHCl$_3$): −23.9°.

The following compounds can be produced in an analogous manner:

4'-{trans-4-[(2R,3S,5R)-5-Heptyl-4-methyl-1,3-dioxan-2-yl]cyclohexyl}-4-[(2R,3S,5R)-5-heptyl-4-methyl-1,3-dioxan-2-yl]biphenyl, 4'-{trans-4-[(2R,3S,5R)-5-hexyl-4-methyl-1,3-dioxan-2-yl]cyclohexyl}-4-[(2R,3S,5R)-5-hexyl-4-methyl-1,3-dioxan-2-yl]biphenyl, 4'-{trans-4-[(2R,3S,5R)-5-nonyl-4-methyl-1,3-dioxan-2-yl]cyclohexyl}-4-[(2R,3S,5R)-5-nonyl-4-methyl-1,3-dioxan-2-yl]biphenyl, 2',3'-difluoro-4'-{trans-4-[(2R,3S,5R)-5-octyl-4-methyl-1,3-dioxan-2-yl]cyclohexyl}-4-[(2R,3S,5R)-5-octyl-4-methyl-1,3-dioxan-2-yl]biphenyl, 2,3-difluoro-4'-{trans-4-[(2R,3S,5R)-5-octyl-4-methyl-1,3-dioxan-2-yl]cyclohexyl}-4-[(2R,3S,5R)-5-heptyl-4-methyl-1,3-dioxan-2-yl]biphenyl, 4'-{2-{trans-4-[(2R,3S,5R)-5-octyl-4-methyl-1,3-dioxan-2-yl]cyclo-hexyl}ethyl}-4-[(2R,3S,5R)-5-octyl-4-methyl-1,3-dioxan-2-yl]biphenyl, 4'-{trans-4-{2-[(2R,3S,5R)-5-octyl-4-methyl-1,3-dioxan-2-yl]ethyl}cyclohexyl}-4-[(2R,3S,5R)-5-octyl-4-methyl-1, 3-dioxan-2-yl]biphenyl, m.p. (C/S$_A$): 88° C., (S$_A$/N*): 98° C., cl.p. (N/I): 184.6° C., 4'-{{trans-4-[(2R,3S,5R)-5-octyl-4-methyl-1,3-dioxan-2-yl]cyclohexyl}methoxy}-4-[(2R,3S,5R)-5-octyl-4-methyl-1,3-dioxan-2-yl]biphenyl, 4'-{2-{trans-4-[(2R,3S,5R)-5-octyl-4-methyl-1,3-dioxan-2-yl]cyclohexyl}ethyl}-4-{2-[(2R,3S,5R)-5-octyl-4-methyl-1,3-dioxan-2-yl]ethyl}biphenyl, 1,4-bis-{trans-4-[(2R,3S,5R)-5-octyl-4-methyl-1,3-dioxan-2-yl]cyclohexyl}benzene, m.p. (C/N*): 106.1° C., cl.p. (N*-I): 222° C., 1,4-bis-{2-{trans-4-[(2R,3S,5R)-5-octyl-4-methyl-1,3-dioxan-2-yl]cyclohexyl}ethyl}benzene and 1,4-bis-{trans-4-{2-[(2R,3S,5R)-5-octyl-4-methyl-1,3-dioxan-2-yl]ethyl}cyclohexyl}benzene.

EXAMPLE 2 a) A mixture of 0.871 g of 4-bromobenzaldehyde, 0.587 g of (2R,3S)-2-octyl-1,3-butanediol (preparation see EP-A-0 457 105) 40 ml of toluene and 8 drops of 2N sulfuric acid was heated under reflux and under nitrogen in a round flask having a magnetic stirrer, water separator and condenser for 15 hours. Then, the mixture was cooled to room temperature, 30 drops of triethylamine were added and the mixture was partitioned between diethyl ether and saturated sodium bicarbonate solution. The organic phases were combined dried over magnesium sulfate, filtered and the filtrate was evaporated. Chromatography of the residue on 140 g of silica gel with 3% ethyl acetate in hexane gave 0.69 g of 1-bromo-4-[(2R,3S,5R)-5-octyl-4-methyl-1,3-dioxan-2-yl]benzene as a brownish oil.

b) A mixture of 1.33 g of 1-bromo-4-[(2R,3S,5R)-5-octyl-4-methyl-1,3-dioxan-2-yl]benzene, 0.3 g of phenyl-1,4-bis-boric acid, 0.077 g of 10% palladium on charcoal, 0.477 g of finely ground sodium carbonate and 20 ml of ethanol was stirred at 90° C. for 100 hours. Then, a further 0.050 g of phenyl-1,4-bis-boric acid, 0.02 g of catalyst and 0.2 g of sodium carbonate were added and the mixture was stirred at 90° C. for a further 15 hours. The reaction mixture was then cooled, filtered over Celite/silica gel and the filtrate was partitioned between diethyl ether and 1N ammonium chloride solution. Thereupon, the organic phases were combined dried over magnesium sulfate, filtered and the filtrate was evaporated. Chromatography of the residue on 200 g of silica gel with 3% ethyl acetate in hexane and subsequent crystallization from hexane gave 0.1 g of 1,4-bis-{4-[(2R,3S,5R)-5-octyl-4-methyl-1,3-dioxan-2-yl]phenyl}benzene as colourless crystals, m.p.: <25° C., S$_G$/S$_C$*: 129.8° C., S$_C$*/N*: 193° C., cl.p. (N*/I): 246.3° C.

The following compounds can be produced in an analogous manner:

1,4-Bis-{4-[(2R,3S,5R)-5-heptyl-4-methyl-1,3-dioxan-2-yl]phenyl}benzene,
1,4-bis-{4-[(2R,3S,5R)-5-hexyl-4-methyl-1,3-dioxan-2-yl]phenyl}benzene,
1,4-bis-{4-[(2R,3S,5R)-5-pentyl-4-methyl-1,3-dioxan-2-yl]phenyl}benzene,
1,4-bis-{4-[(2R,3S,5R)-5-nonyl-4-methyl-1,3-dioxan-2-yl]phenyl}benzene,
1,4-bis-{4-[(2R,3S,5R)-5-decyl-4-methyl-1,3-dioxan-2-yl]phenyl}benzene,
1-{4-[(2R,3S,5R)-5-heptyl-4-methyl-1,3-dioxan-2-yl]phenyl}-4-{4-[(2R,3S,5R)-5-octyl-4-methyl-1,3-dioxan-2-yl]phenyl}-benzene,
1,4-bis-{4-[(2R,3S,5R)-5-(7-octenyl)-4-methyl-1,3-dioxan-2-yl]phenyl}benzene,
1,4-bis-{4-[(2R,3S,5R)-5-octyl-4-methyl-1,3-dioxan-2-yl]phenyl}-2,3-difluorobenzene,
1,4-bis-{3-fluoro-4-[(2R,3S,5R)-5-(7-octenyl)-4-methyl-1,3-dioxan-2-yl]phenyl}benzene,
1,4-bis-{2-fluoro-4-[(2R,3S,5R)-5-(7-octenyl)-4-methyl-1,3-dioxan-2-yl]phenyl}benzene,
1-{2,3difluoro-4-[(2R,3S,5R)-5-(7-octenyl)-4-methyl-1,3-dioxan-2-yl]phenyl}-4-{4-[(2R,3S,5R)-5-(7-octenyl)-4-methyl-1,3-dioxan-2-yl]phenyl}benzene and
1,4-bis-{4-{2-[(2R,3S,5R)-5-octyl-4-methyl-1,3-dioxan-2-yl]ethyl}phenyl]benzene, m.p. (S/A$_A$): 140.2° C., (S$_A$/N*): 175° C., cl.p. (N*/I): 181.8° C.

EXAMPLE 3

1.2 g of N,N'-dicyclohexylcarbodiimide are added portionwise within 10 minutes while stirring to a solution of 2.05 g of 4-{4-[(2R,3S,5R)-5-octyl-4-methyl-1,3-dioxan-2-yl]phenyl}benzoic acid, 1.4 g of 4-[(2R,3S,5R)-5-octyl-4-methyl-1,3-dioxan-2-yl]phenol and 0.1 g of 4-(dimethylamino)pyridine in 250 ml of dichloromethane. The mixture is stirred at room temperature overnight and then filtered. The filtrate is diluted with dichloromethane, washed twice with 50 ml of saturated sodium carbonate solution each time and then with water, dried over magnesium sulfate, filtered and the filtrate is concentrated. Chromatography of the residue on silica gel with toluene and recrystallization from hexane gives 4'-[(2R,3S,5R)-5-octyl-4-methyl-1,3-dioxan-2-yl]biphenylcarboxylic acid 4-[(2R,3S,5R)-5-octyl-4-methyl-1,3-dioxan-2-yl]phenyl ester: m.p. (C/S$_A$): 95.6° C., (S$_A$/N*): 106.6° C., cl.p. (N*/I) 234° C.

The following compounds can be produced in an analogous manner:

4'-[(2R,3S,5R)-5-Octyl-4-methyl-1,3-dioxan-2-yl]biphenylcarboxylic acid 4-[(2R,3S,5R)-5-nonyl-4-methyl-1,3-dioxan-2-yl]phenyl ester,
4'-[(2R,3S,5R)-5-nonyl-4-methyl-1,3-dioxan-2-yl]biphenylcarboxylic acid 4-[(2R,3S,5R)-5-hyptyl-4-methyl-1,3-dioxan-2-yl]phenyl ester,
4'-[(2R,3S,5R)-5-octyl-4-methyl-1,3-dioxan-2-yl]biphenylcarboxylic acid 4-[(2R,3S,5R)-5-(7-octenyl)-4-methyl-1,3-dioxan-2-yl]phenyl ester,
4'-[(2R,3S,5R)-5-(7-octenyl)-4-methyl-1,3-dioxan-2-yl]biphenylcarboxylic acid 4-[(2R,3S,5R)-5-octyl-4-methyl-1,3-dioxan-2-yl]phenyl ester,
2,3-difluoro-4'-[(2R,3S,5R)-5-octyl-4-methyl-1,3-dioxan-2-yl]biphenylcarboxylic acid 4-[(2R,3S,5R)-5-octyl-4-methyl-1,3-dioxan-2-yl]phenyl ester,
2',3'-difluoro-4'-[(2R,3S,5R)-5-octyl-4-methyl-1,3-dioxan-2-yl]biphenylcarboxylic acid 4-[(2R,3S,5R)-5-octyl-4-methyl-1,3-dioxan-2-yl]phenyl ester,
4-[(2R,3S,5R)-5-octyl-4-methyl-1,3-dioxan-2-yl]benzoic acid 4'-[(2R,3S,5R)-5-octyl-4-methyl-1,3-dioxan-2-yl]biphenyl ester, m.p. (C/S$_A$): 114.1° C., (S$_A$/N*): 128.5° C., cl.p. (N*/I): 230.6° C.,
4-[(2R,3S,5R)-5-octyl-4-methyl-1,3-dioxan-2-yl]benzoic acid 4-{trans-4-[(2R,3S,5R)-5-octyl-4-methyl-1,3-dioxan-2-yl]cyclohexyl}phenyl ester and
4-{trans-4-[(2R,3S,5R)-5-octyl-4-methyl-1,3-dioxan-2-yl]cyclohexyl}benzoic acid 4-[(2R,3S,5R)-5-octyl-4-methyl-1,3-dioxan-2-yl]phenyl ester.

EXAMPLE 4

Test mixtures each with the two basic mixtures BM-I and BM-II were prepared in order to investigate the properties of the compounds of formula I in mixtures. GM-I is an achiral (non-doped) mixture and serves to determine the phase sequence, especially the extent of the $S_C^*$ phase transition, as well as the spontaneous polarization (Ps). GM-II is a chiral doped mixture and serves to measue the wavelength of the selective reflection ($\lambda_{sel}$). This is a measurement for the helical pitch, that is, the smaller the measured value for $\lambda_{sel}$ is, then the smaller is the pitch and the stronger is the twisting capacity of the dopant. Moreover, two comparative mixtures were prepared for comparison purposes. For this purpose, the two basic mixtures GM-I and GM-II were each doped with a tetranuclear chiral bis-methyldioxane.

The measurements were carried out under the following conditions: Ps measurements at about 8 m$\mu$ cell thickness and a delta voltage of 10 Hz and 5 V/$\mu$. Measurements of $\lambda_{sel}$ with homeotroptic orientation. A temperature of 25° C. was observed for all measurements.

Basic mixture I (BM-I)
7.0 wt. % of 5-(5-heptyl-1,3-dioxan-2-yl)-2-(4-octyloxyphenyl)pyridine;
7.0 wt. % of 5-(5-octyl-1,3-dioxan-2-yl)-2-(4-octyloxyphenyl)pyridine;
6.0 wt. % of 5-(5-decyl-1,3-dioxan-2-yl)-2-(4-octylphenyl) pyridine;
15.9 wt. % of 4-decyloxybenzoic acid 4-[2-(trans-4-pentylcyclohexyl)ethyl]phenyl ester;
7.1 wt. % of 4-dodecyloxybenzoic acid 4-[2-(trans-4-pentylcyclohexyl)ethyl]phenyl ester;
7.0 wt. % of 2,3-difluoro-4-undecyloxybenzoic acid 4-[2-(trans-4-pentylcyclohexyl)ethyl]phenyl ester;
14.9 wt. % of 2-(4-hexyloxyphenyl)-5-nonylpyrimidine;
19.9 wt. % of 2-(4-nonyloxyphenyl)-5-nonylpyrimidine;
5.0 wt. % of 2-(4-octyloxyphenyl)-5-heptylpyrimidine;
10.1 wt. % of 2-(4-hexyloxyphenyl)-5-octylpyrimidine;
Phase sequence: I-103° C.-N-80° C.-$S_A$-76.5° C.-$S_C$-−17.5° C. C Comparative mixture I
7.0 wt. % of 1,4-bis-{4-[(2R,3S,5R)-5-octyl-4-methyl-1,3-dioxan-2-yl]}benzene
93.0 wt. % of BM-I
sequence: I-104.0° C.-N*-67.4° C.-$S_C^*$-;
Ps: 10.1 nC/cm$^2$ Test mixture I-1
7.0 wt. % of 1,4-bis-{4-[(2R,3S,5R)-5-octyl-4-methyl-1,3-dioxan-2-yl]phenyl}benzene
93.0 wt. % of BM-I
sequence: I-109.4° C.-N*-80° C.-$S_A$-72.9° C.-$S_C^*$-;
Ps: 13.1 nC/cm$^2$ Test mixture I-2
7.0 wt. % of 4'-{trans-4-[(2R,3S,5R)-5-octyl-4-methyl-1,3-dioxan-2-yl]cyclohexyl}-4-[(2R,3S,5R)-5-octyl-4-methyl-1,3-dioxan-2-yl]biphenyl
93.0 wt. % of BM-I
sequence: I-110.1° C.-N*-72.0° C.-$S_C^*$-;
Ps: 11.5 nC/cm$^2$ Basic mixture II (BM-II)
27.0 wt. % of 1,4-bis-{4-[(S)-2-octyloxy]phenyl}benzene
15.7 wt. % of 2-(4-octyloxyphenyl)-5-[(4E)-4-octenoyloxy] pyrimidine;
5.2 wt. % of 2-(4-octanoyloxyphenyl)-5-octylpyridine;
5.2 wt. % of 2-{4-[(2E)-2-octenoyloxy]phenyl}-5-heptylpyridine;
5.2 wt. % of 2-{4-[(2E)-2-octenoyloxy]phenyl}-5-octylpyridine;
10.4 wt. % of 2-(4-heptylphenyl)-5-[(2E)-2-octenyloxy] pyrimidine;
15.6 wt. % of 2-(4-hexyloxyphenyl)-5-nonylpyrimidine;
15.6 wt. % of 2-(4-nonyloxyphenyl)-5-nonylpyrimidine;
$\lambda_{sel}$: 508 nm Comparative mixture II
3.0 wt. % of 1,4-bis-{4-[(2R,3S,5R)-5-octyl-4-methyl-1,3-dioxan-2-yl]}benzene
93.0 wt. % of BM-I
$\lambda_{sel}$: 437 nm Test mixture II-1
3.0 wt. % of 1,4-bis-{4-[(2R,3S,5R)-5-octyl-4-methyl-1,3-dioxan-2-yl]phenyl}benzene
97.0 wt. % of BM-II
$\lambda_{sel}$: 404 nm Test mixture II-2
3.0 wt. % of 4'-{trans-4-[(2R,3S,5R)-5-octyl-4-methyl-1,3-dioxan-2-yl]cyclohexyl}-4-[(2R,3S,5R)-5-octyl-4-methyl-1,3-dioxan-2-yl]biphenyl
97.0 wt. % of BM-II
$\lambda_{sel}$: 414 nm

What is claimed is:

1. A compound of the formula

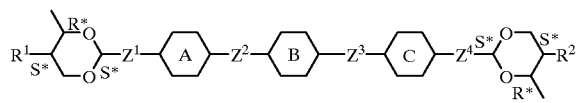

I

R$^1$ and R$^2$ each independently are alkyl or alkenyl; alkyl or alkenyl in which one methylene group is replaced by —O—, —COO—, or —OOC—; alkyl or alkenyl in which two non-adjacent methylene groups are replaced by —O—, —COO—, or —OOC—; alkyl or alkenyl in which at least one hydrogen atom is replaced by fluorine, chlorine, or cyano; alkyl or alkenyl in which one methylene group is replaced by —O—, —COO—, or —OOC— and at least one hydrogen atom is replaced by fluorine, chlorine, or cyano; or alkyl or alkenyl in which two non-adjacent methylene groups are replaced by —O—, —COO—, or —OOC— and at least one hydrogen atom is replaced by fluorine, chlorine or cyano;

one of rings A, B and C is a 1,4-phenylene which is unsubstituted or substituted with 1 or 2 fluorine atoms and the other two rings each independently are 1,4-phenylene which is unsubstituted or substituted with 1 or 2 fluorine atoms or trans-1,4-cyclohexylene;

Z$^1$ and Z$^4$ each are a single bond;

Z$^2$ and Z$^3$ each are a single bond; and

R* and S* signify that the denoted carbon have the (R) configuration or its optical antipode or the (S) configuration or its optical antipode.

2. A compound according to claim 1, wherein rings A, B and C each independently are 1,4-phenylene, 2- or 3-fluoro-1,4-phenylene, or 2-3-difluoro-1,4-phenylene.

3. A compound according to claim 1, wherein one of rings A, B and C is 1,4-phenylene, 2- or 3-fluoro-1,4-phenylene or 2,3-difluoro-1,4-phenylene and the other rings each independently are 1,4-trans-cyclohexylene, 1,4-phenylene, 2- or 3-fluoro-1,4-phenylene or 2,3-difluoro-1,4-phenylene.

4. A compound according to claim 1, of one of the formulas

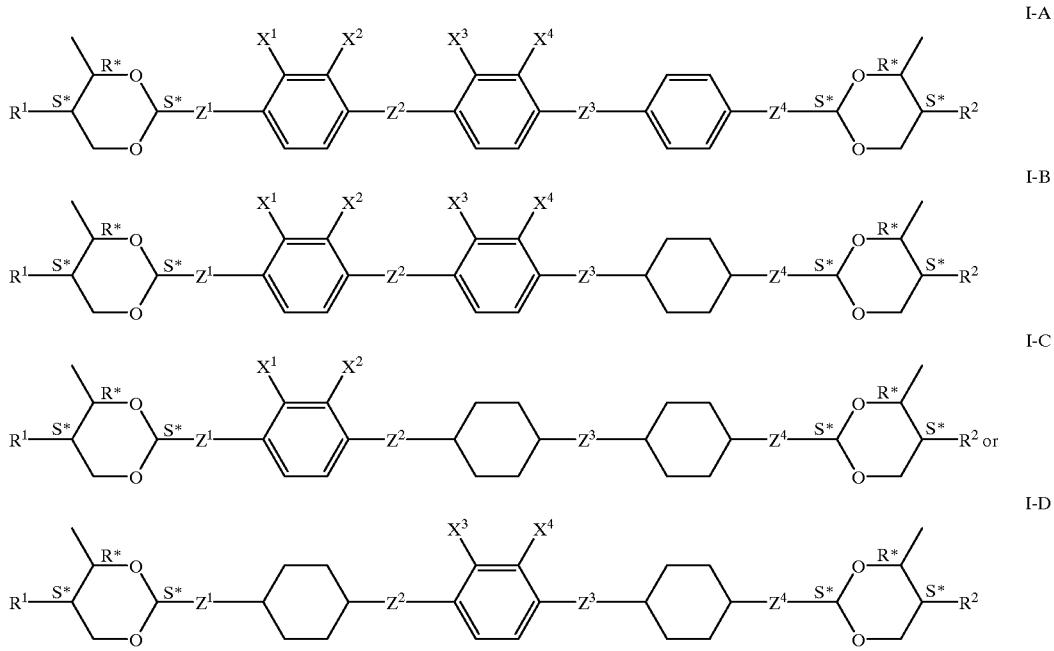

wherein
- $R^1$ and $R^2$ each independently are $C_1$–$C_{12}$ alkyl or $C_2$–$C_{12}$ alkenyl; or $C_1$–$C_{12}$ alkyl or $C_2$–$C_{12}$ alkenyl in which one methylene group is replaced by —O—, —COO— or —OOC—:
- $Z^1$ and $Z^4$ each are a single bond;
- $Z^2$ and $Z^3$ are each a single bond, and the substituents $X^1$ to $X^4$ each independently are hydrogen or fluorine.

5. A compound according to claim 4, of the formula

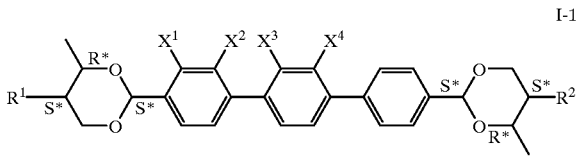

I-1 wherein
- $R^1$ and $R^2$ each independently are $C_1$–$C_{12}$ alkyl or $C_2$–$C_{12}$ alkenyl; or $C_1$–$C_{12}$ or alkenyl in which one methylene group is replaced by —O—, —COO— or —OOC—; and
- $X^1$ to $X^4$ each independently are hydrogen or fluorine.

6. A compound according to claim 5, wherein no more than two of the groups $X^1$, $X^2$, $X^3$ and $X^4$ are fluorine.

7. A compound according to claim 4, of the formula

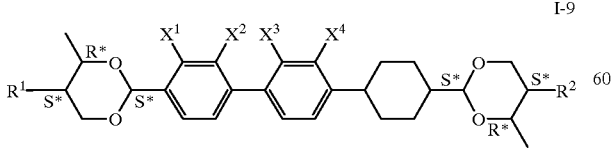

I-9 wherein
- $R^1$ and $R^2$ each independently are $C_1$–$C_{12}$ alkyl or $C_2$–$C_{12}$ alkenyl; or $C_2$–$C_{12}$ alkyl or $C_2$–$C_{12}$ alkenyl in which one methylene group is replaced by —O—, —COO— or —OOC—; and
- $X^1$ to $X^4$ each independently are hydrogen or fluorine.

8. A compound according to claim 7, wherein no more than two of the groups $X^1$, $X^2$, $X^3$ and $X^4$ are fluorine.

9. A compound according to claim 4, of the formula

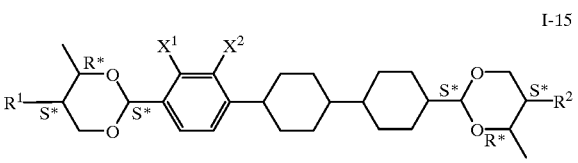

I-15 wherein
- $R^1$ and $R^2$ each independently are $C_1$–$C_{12}$ alkyl or $C_2$–$C_{12}$ alkenyl; or $C_1$–$C_{12}$ alkyl or $C_2$–$C_{12}$ alkenyl in which one methylene group is replaced by —O—, —COO— or —OOC—; and
- $X^1$ to $X^4$ each independently are hydrogen or fluorine.

10. A compound according to claim 9, wherein no more than two of the groups $X^1$, $X^2$, $X^3$ and $X^4$ are fluorine.

11. A compound according to claim 4, of the formula

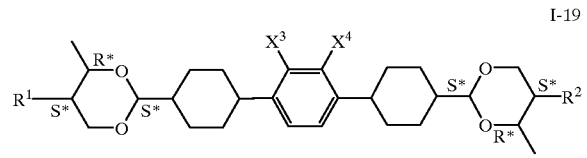

I-19 wherein
- $R^1$ and $R^2$ each independently are $C_1$–$C_{12}$ alkyl or $C_2$–$C_{12}$ alkenyl; or $C_1$–$C_{12}$ alkyl or $C_2$–$C_{12}$ alkenyl in which one methylene group is replaced by —O—, —COO— or —OOC—; and
- $X^1$ to $X^4$ each independently are hydrogen or fluorine.

12. A compound according to claim 11, wherein no more than two of groups $X^1$, $X^2$, $X^3$ and X4 are fluorine.

13. A liquid crystalline mixture comprising a carrier material and at least one optically active compound of formula I

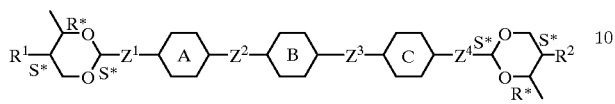

$R^1$ and $R^2$ each independently are alkyl or alkenyl; alkyl or alkenyl in which one methylene group is replaced by —O—, —COO—, or —OOC—; alkyl or alkenyl in which two non-adjacent methylene groups are replaced by —O—, —COO—, or —OOC—; alkyl or alkenyl in which at least one hydrogen atom is replaced by fluorine, chlorine, or cyano; alkyl or alkenyl in which one methylene group is replaced by —O—, —COO—, or —OOC— and at least one hydrogen atom is replaced by fluorine, chlorine, or cyano; or alkyl or alkenyl in which two non-adjacent methylene groups are replaced by —O—, —COO—, or —OOC— and at least one hydrogen atom is replaced by fluorine, chlorine or cyano;

one of rings A, B and C is a 1,4-phenylene which is unsubstituted or substituted with 1 or 2 fluorine atoms and the other two rings each independently are 1,4-phenylene which is unsubstituted or substituted with 1 or 2 fluorine atoms or trans-1,4-cyclohexylene;

$Z^1$ and $Z^4$ each are a single bond;

$Z^2$ and $Z^3$ each are a single bond; and

R* and S* signify that the denoted carbon have the (R) configuration or its optical antipode or the (S) configuration or its optical antipode.

14. A liquid crystalline mixture in accordance with claim 13, wherein the content of optically active compounds of formula I is 1–30 wt. %.

15. An electro-optical device comprising the compound

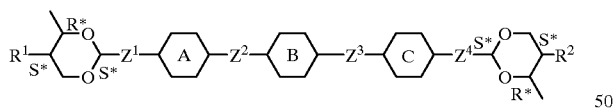

$R^1$ and $R^2$ each independently are alkyl or alkenyl; alkyl or alkenyl in which one methylene group is replaced by —O—, —COO—, or —OOC—; alkyl or alkenyl in which two non-adjacent methylene groups are replaced by —O—, —COO—, or —OOC—; alkyl or alkenyl in which at least one hydrogen atom is replaced by fluorine, chlorine, or cyano; alkyl or alkenyl in which one methylene group is replaced by —O—, —COO—, or —OOC— and at least one hydrogen atom is replaced by fluorine, chlorine, or cyano; or alkyl or alkenyl in which two non-adjacent methylene groups are replaced by —O—, —COO—, or —OOC— and at least one hydrogen atom is replaced by fluorine, chlorine or cyano;

one of rings A, B and C is a 1,4-phenylene which is unsubstituted or substituted with 1 or 2 fluorine atoms and the other two rings each independently are 1,4-phenylene which is unsubstituted or substituted with 1 or 2 fluorine atoms or trans-1,4-cyclohexylene;

$Z^1$ and $Z^4$ each are a single bond;

$Z^2$ and $Z^3$ each are a single bond; and

R* and S* signify that the denoted carbon have the (R) configuration or its optical antipode or the (S) configuration or its optical antipode.

16. An electro-optical device comprising a carrier material and at least one optically active compound of formula I

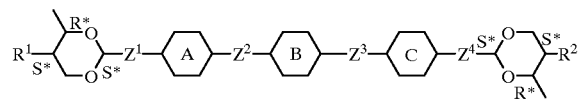

$R^1$ and $R^2$ each independently are alkyl or alkenyl; alkyl or alkenyl in which one methylene group is replaced by —O—, —COO—, or —OOC—; alkyl or alkenyl in which two non-adjacent methylene groups are replaced by —O—, —COO—, or —OOC—; alkyl or alkenyl in which at least one hydrogen atom is replaced by fluorine, chlorine, or cyano; alkyl or alkenyl in which one methylene group is replaced by —O—, —COO—, or —OOC— and at least one hydrogen atom is replaced by fluorine, chlorine, or cyano; or alkyl or alkenyl in which two non-adjacent methylene groups are replaced by —O—, —COO—, or —OOC— and at least one hydrogen atom is replaced by fluorine, chlorine or cyano;

one of rings A, B and C is a 1,4-phenylene which is unsubstituted or substituted with 1 or 2 fluorine atoms and the other two rings each independently are 1,4-phenylene which is unsubstituted or substituted with 1 or 2 fluorine atoms or trans-1,4-cyclohexylene;

$Z^1$ and $Z^4$ each are a single bond;

$Z^2$ and $Z^3$ each are a single bond; and

R* and S* signify that the denoted carbon have the (R) configuration or its optical antipode or the (S) configuration or its optical antipode.

* * * * *